United States Patent [19]
Weston

[11] Patent Number: 4,968,143
[45] Date of Patent: Nov. 6, 1990

[54] PORTABLE SPECTROPHOTOMETER

[75] Inventor: Allen Weston, Lugano, Switzerland

[73] Assignee: Maxmeyer-Duco MM.D S.p.A., Milan, Italy

[21] Appl. No.: 331,133

[22] Filed: Mar. 31, 1989

[30] Foreign Application Priority Data

Mar. 31, 1988 [IT] Italy .............................. 20067 A/88

[51] Int. Cl.[5] .............................................. G01J 3/42
[52] U.S. Cl. .................................. 356/328; 356/236; 250/228
[58] Field of Search ............... 356/319, 326, 328, 236; 250/228

[56] References Cited

U.S. PATENT DOCUMENTS 3,923,399 12/1975 Brumley .............................. 356/328

OTHER PUBLICATIONS

Kishner, Conference: Proceedings of the Third Congress of the International Colour Association, Troy, N.Y. U.S.A., (10–15 Jul. 1977) pp. 305–308.
Myrab et al., *Applied Optics*, vol. 2, No. 15, Aug. 1, 1982, pp. 2855–2858.

*Primary Examiner*—F. L. Evans
*Attorney, Agent, or Firm*—Fleit, Jacobson, Cohn, Price, Holman & Stern

[57] ABSTRACT

A portable spectrophotometer is disclosed which is provided with a holding case accommodating opto-mechanical color-reading devices and an electronic control device provided with a microprocessor having data and program memories. The spectrophotometer further includes a power source which enables its self-sustained field use.

2 Claims, 5 Drawing Sheets

PORTABLE SPECTROPHOTOMETER

DESCRIPTION

This invention relates to a spectrophotometer particularly, but not exclusively useful to analyse the color of such articles of manufacture as the bodyworks of passenger cars and generic motor vehicles, in order to enable reproduction thereof.

It is a known fact that repair work on the bodies of motor vehicles, such as passenger cars, trucks, and the like, involves the ability to reproduce as faithfully as possible the color of a motor vehicle in view of its re-painting on completion of the repairs to its bodywork.

The paint that protects the bodywork of a motor vehicle undergoes, in fact, various hue alterations as a result of ageing processes as brought about, as is well recognized, by the actions of sunlight and/or weathering, or of washing and the frequency of such washing. Accordingly, the paint color is bound to undergo in time inevitable changes which are difficult to foresee and make it different from that originally imparted to the vehicle.

It follows that the so-called original paint supplied by the vehicle manufacturer is in all cases unsuited to provide a faithful replica of the color actually exhibited by the individual article.

Thus, to provide a solution to the problem, there have been developed in the art more or less complex instruments capable of outputting an "as is" paint recipe which is then prepared by blending together such paints as may be available commercially at the time.

To that end, the reflected light from the article surface, or in other terms its color, is usually analysed on a spectrophotometer, i.e. split into its spectral components for subsequent qualitative and quantitative measurement on so-called bench spectrophotometers.

The latter instruments, while providing a very accurate measurement of the spectral components of the color being analysed, are highly complex and large in size, quite expensive, and high in energy consumption.

Bench spectrophotometers tend, therefore, to be configured as typical laboratory instruments, indeed quite accurate but far from providing those features of flexibility in use, ease of transportation, and low cost as have long been sought by car bodywork repairers.

The size of such bench instruments results in their being unsuitable for use outside of a workshop and/or laboratory, directly on the involved motor vehicle. Thus, the need arises for picking up, using sometimes destructive techniques, a sample from a bodywork to be re-painted.

To obviate the above drawbacks of bench instruments, there have been proposed in the pertinent art spectrophotometers which can be carried around and used in the field.

Instruments of that type include a reading head connected by a flexible cable to a data processing unit equipped with a variety of accessories, such as a printer for a printed output of the measured data.

However, spectrophotometers of the last-mentioned type can only be moved with some difficulty due to their being made up of parts having a significant weight which are to be interconnected by means of a linking cable.

The latter requirement restricts their usability in the field on account of the reading head and processing unit, which are unseparable, being inconvenient and laborious to carry.

A further drawback of such prior instruments is their cost; this being even higher than that of bench spectrophotometers, is generally beyond the reach of an average user.

The technical problem underlying this invention is to provide a spectrophotometer which is portable and has such constructional and operational features as to permit of "as is" reproduction of an analysed color, while overcoming the cited draw affecting the prior art.

This problem is solved according to the invention by a portable spectrophotometer provided with a holding case being characterized in that it comprises, all located inside said case:

a light source connected, via a control circuit, to an output of a microprocessor having data (RAM) and program (ROM) storages;

a sphere effective to make the luminous flux exiting said case more uniform;

a spectroscope for spectrum-wise scattering the reflected light from a sample illuminated by said source to a photometric device connected to the input end of said microprocessor via an analog-to-digital converter;

an optical device for illuminating said photometric device directly from said light source;

a power supply to the light source, photometric device, control circuit, analog-to-digital converter, and microprocessor; and a connector for connecting the microprocessor to the outside of said case.

Further features and the advantages of a spectrophotometer according to this invention will be more clearly understood from the following detailed description of an embodiment thereof, to be taken by way of illustration and not of limitation in conjunction with the accompanying drawings, where:

Figure 1:
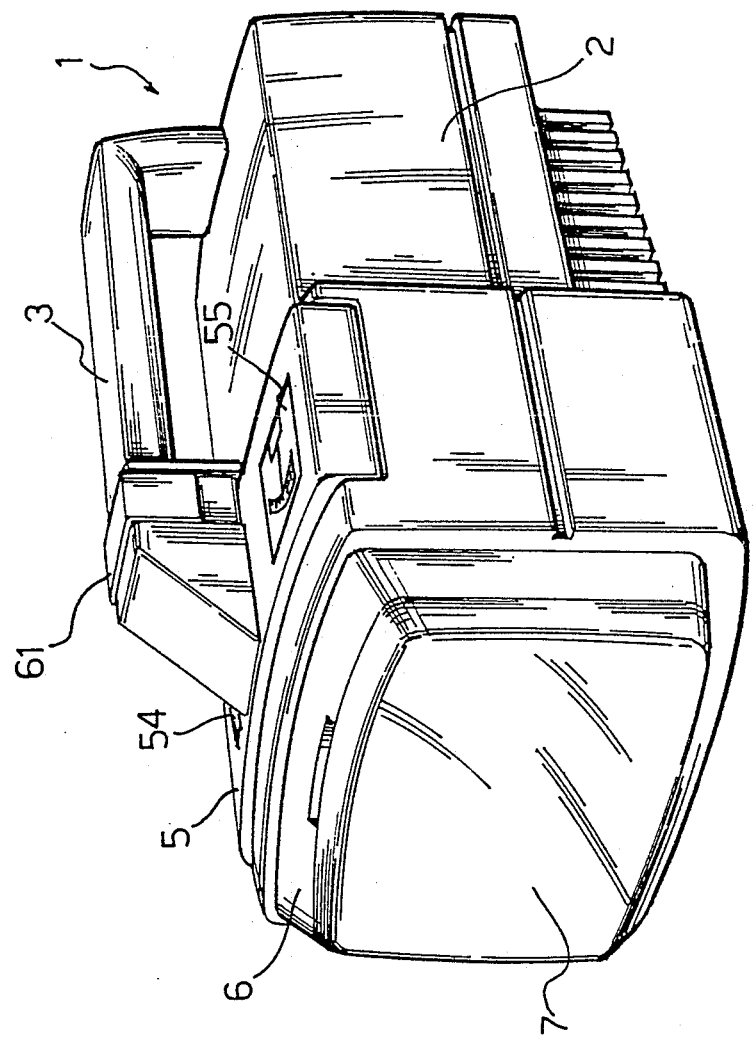
FIG. 1 shows in perspective a portable spectrophotometer according to the invention.

With reference to the drawing views, generally indicated at 1 is a portable spectrophotometer according to this invention.

The spectrophotometer 1 comprises a substantially parallelepipedic holding case 2 enclosing opto-mechanical devices 60 and an electronic control device 63, both to be explained hereinafter.

The case 2 is provided with a carrying handle 3 at the top, and with a bottom 18 having plural rest feet 4.

Figure 2:
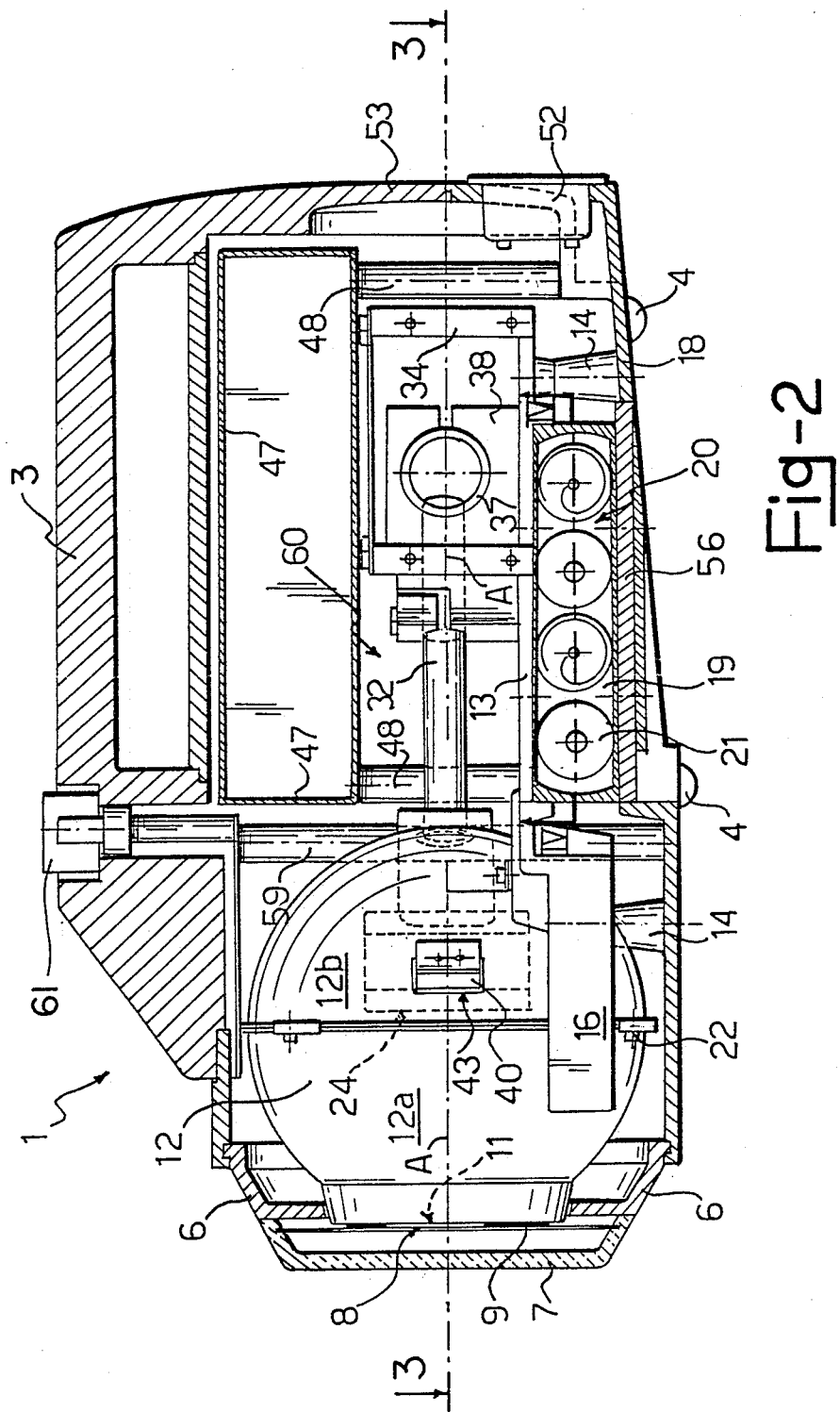
FIG. 2 is a longitudinal section view taken through the spectrophotometer of FIG. 1 along the line II—II in FIG. 3.

The case 2 further comprises a reading head 5, substantially parallelepipedic in shape, provided on the front with a basically frusto-pyramidal holder 6 for a circular cross-section reading eye 8 which is protected on the front by a plate-like cover 7 (see FIG. 2).

The reading eye 8 comprises a circular cross-section aperture 11 formed in a hollow sphere 12 effective to make the density more uniform of the luminous flux exiting the reading head 5 through the reading eye 8, as explained hereinafter.

The latter is provided peripherally with a ring magnet 9 to enhance the adhesion of the reading head 5 on a metal surface to be analysed.

With reference to FIG. 2, it should be noted that the spectrophotometer opto-mechanical devices are carried inside the case 2 on a plate 13 having a substantially rectangular contour and being laid onto a plurality of spacers 14 standing integrally proud of the bottom 18 of the case 2, to which spacers it is fastened by means of conventional screw fasteners, not shown.

Figure 4:
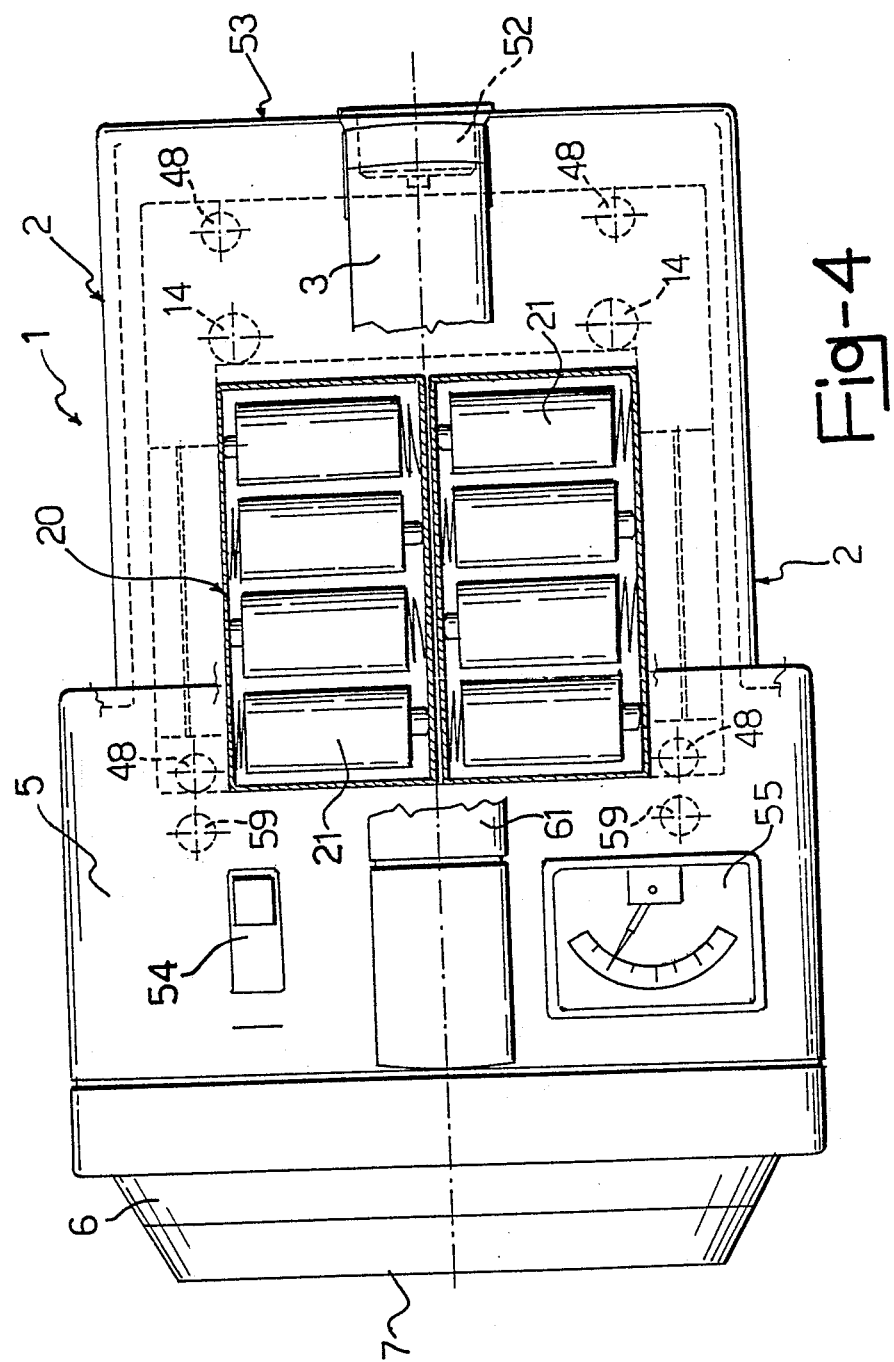
FIG. 4 is a plan view, partly sectioned along the line IV-IV in FIG. 2, of the spectrophotometer of FIG. 1.

Thus, there is defined, between said plate 13 and the bottom 18 of the case, a substantially parallelepipedic chamber 19 intended to accommodate a power supply 20 comprising a battery 21 (see FIGS. 2 and 4).

Said chamber 19 is accessible from the outside via a cover 56 attached removably to the bottom 18 of the case 2 by means of conventional screw fasteners, not shown.

With reference to FIG. 2, note should be taken of that the case 2 is provided, inside the reading head 5 and in the proximity of the sphere 12, with a pair of posts 59 which stiffen its structure making the construction of the spectrophotometer stronger.

The plate 13 is provided at one end with a yoke portion 16 holding the sphere 12, conventionally fastened thereto by means of screws 17.

To improve its stability, the sphere 12 is caused to bear on a seat 58 mating in profile with the outer surface of the sphere.

The sphere 12 (FIGS. 2 and 3) comprises two emispherical portions, respectively a front one 12a and rear one 12b, which are fastened removably together in a conventional manner, such as by a plurality of screws 22.

Figure 3:
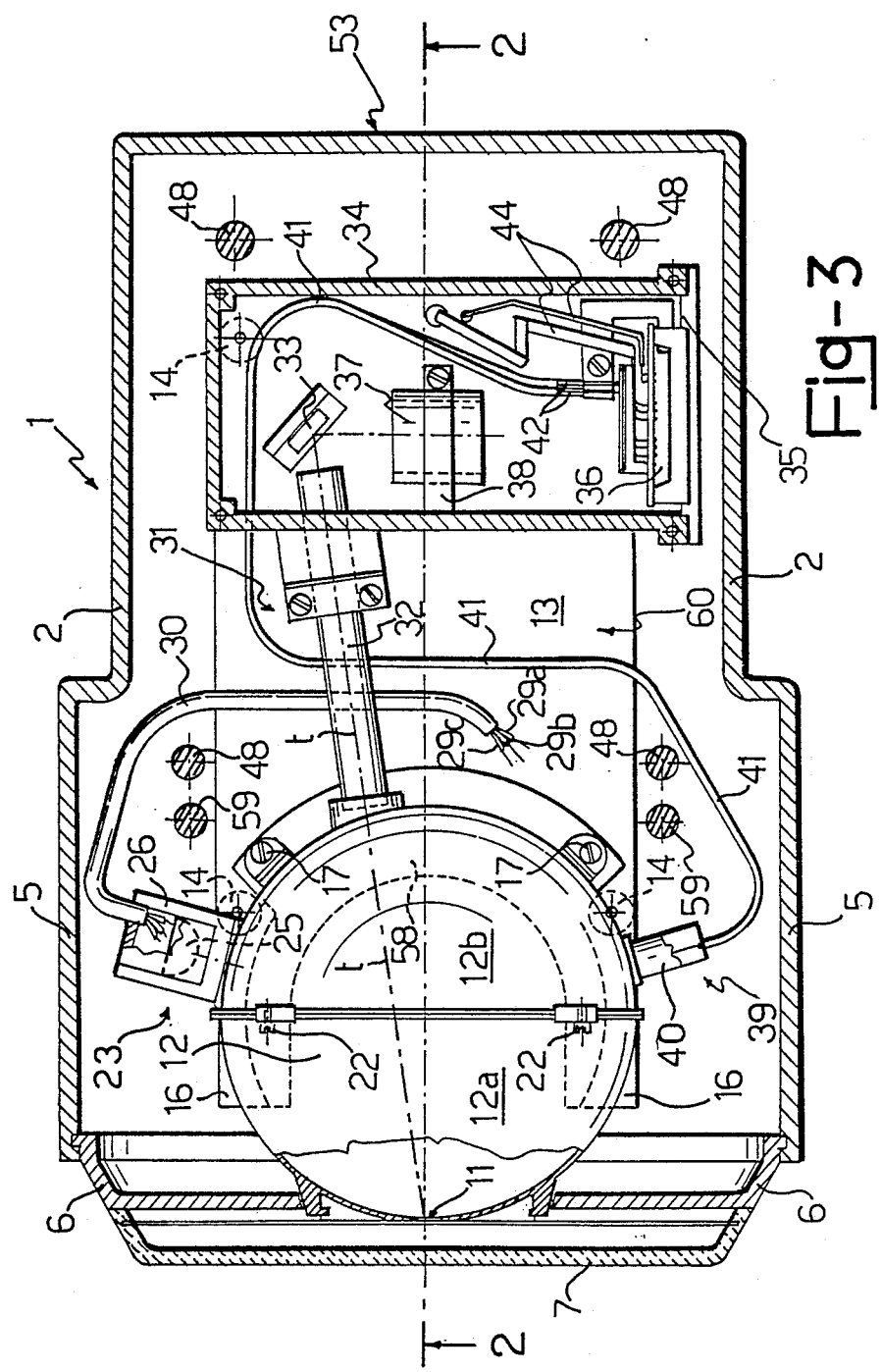
FIG. 3 is a longitudinal section view taken through the spectrophotometer of FIG. 1 along the line III—III in FIG. 2.

For illuminating the surface of an article to be analysed, the spectrophotometer 1 is provided with a light source 23 conventionally mounted to the rear emispherical portion 12b of the sphere 12 close to the area of the joint to the front portion 12a (see FIG. 3). The light source 23 includes a flash bulb 25 fitting in a respective prismatic container 26 which opens into the sphere 12 at a passageway 24 of rectangular cross-sectional shape extending into the sphere 12 symmetrically about a horizontal diametral plane A—A thereof (see FIG. 2).

The flash bulb 25 enables the surface being analysed to be illuminated with light flashes having a color temperature of about 6000 K.

Figure 5:
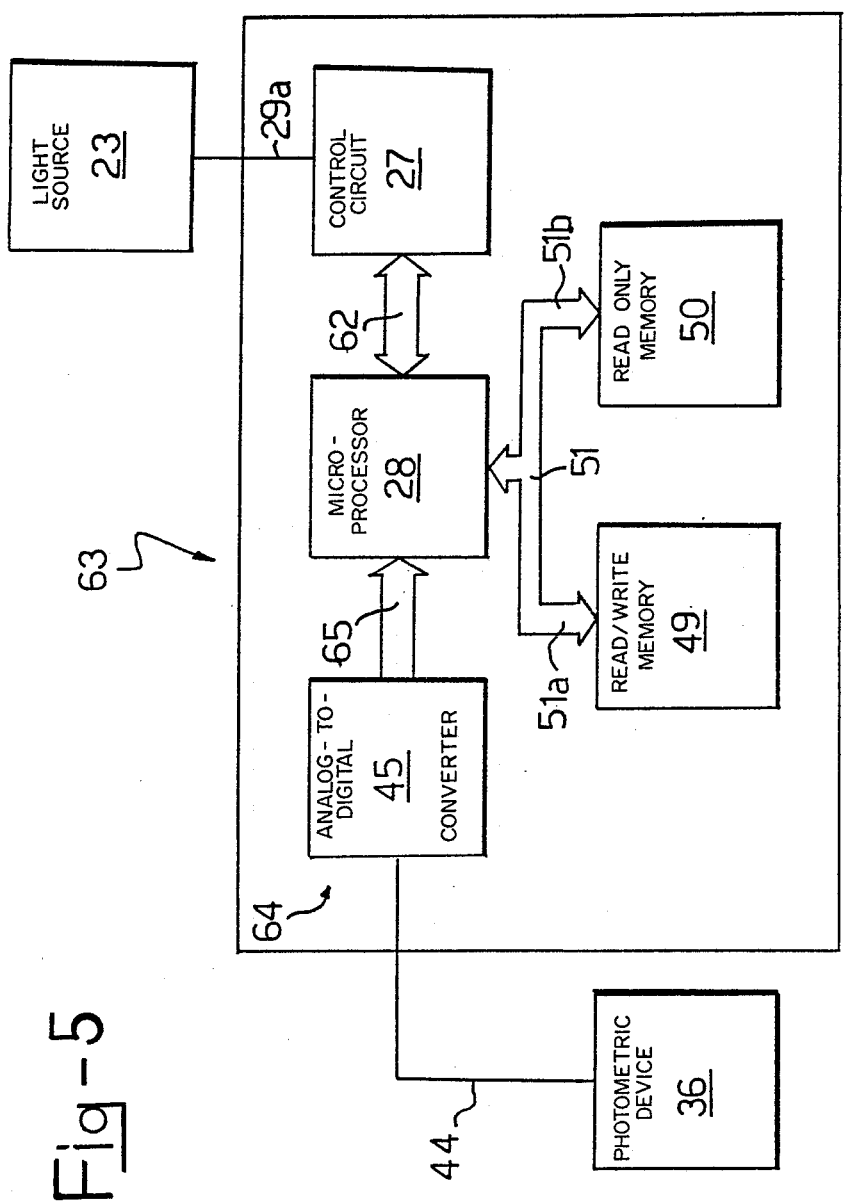
FIG. 5 is a block diagram of an electronic control device incorporated to the spectrophotometer of FIG. 1.

According to one aspect of this invention, and as shown diagramatically in FIG. 5, the light source 23 is connected by a cable 29a to the output of a conventional control circuit 27, in turn connected to an output of a microprocessor 28, also to a conventional design, by means of a bus conductor 62.

Thus, the light source 23 is linked operatively to the microprocessor 28 via said control circuit 27.

The light source 23 itself is powered, via another pair of cables 29b, 29c enclosed, along with the cable 29a, in a sheath 30, from the power supply 20 located in the chamber 19 defined between the holding plate 13 and the bottom 18 of the case 2.

The flash bulb 25 is turned on, and the ensuing analysis operation for color carried out, under external control by depressing a key 61 which straddles the carrying handle 3 above the reading head 5 and is conventionally connected to the microprocessor 28 in a manner not shown.

The opto-mechanical devices of the spectrophotometer 1 also comprise (see FIGS. 2 and 3) a spectroscope 31 for spectrum-wise scattering the reflected light from the article surface illuminated by the light source 23.

The spectroscope 31 comprises a collimator 32 and a diffraction grating 33. The collimator 32 is provided with a set of conventional lenses, not shown, the optical axis t—t whereof intersects the center of the aperture 11 in the sphere 12, as shown in FIG. 3.

The grating 33 is accommodated within a box-type protective housing 34, substantially parallelepipedic in shape, and laid in continuation of the optical axis t—t of the collimator 32 to form an angle of about 45° therewith.

The box-type housing 34 is conventionally supported on the plate 13 (e.g. welded thereto), and is formed, at a minor base thereof, with an aperture 35 which is shut off by a photometric device 36 attached to the holding plate 13 in just a conventional manner, not illustrated.

In order to enhance the optical resolution of the spectral components of the light diffracted by the grating 33, a focusing objective 37 is interposed to said grating and the photometric device 36 (FIG. 3).

The objective 37 is supported, as shown in FIGS. 2 and 3, on the box-type housing 34 and the plate 13 via a respective sheet-like holder 38.

With reference to FIG. 2, it should also be noted that the axes of the aperture 11, collimator 32, and objective 37 all lie in the same horizontal plane A—A the outline whereof is shown in the Figure for clarity.

The photometric device 36 comprises a plurality of conventional photocells, omitted from the drawings, for qualitatively and quantitatively picking up the spectral components of the reflected light from the article surface. To this end, this same light is resolved by the grating 33 into a diffraction beam whose width encompasses on the whole a wavelength band from 400 to 700 nm.

The diffraction beam thus obtained can be advantageously sampled by the photometric device 36 in a recordable manner, according to wavelength ranges which lie between about 10 nm and about 20 nm, to be selected from the outside via the microprocessor 28.

With reference to FIG. 3, it may be seen that the light source 23 is connected optically to the input end of the photometric device 36 by means of an optical device 39 comprising a light-responsive element 40 and a flexible cable 41 having a pair of fiber optics 42.

Thus, the photometric device 36 is supplied a second, reference light beam intended for comparison, as explained herein below, to the light beam reflected from the sample and scattered into its spectral components by the spectroscope 31.

The light-responsive element 40 constitutes, therefore, as a reference internal to the spectrophotometer; for this purpose, it is arranged to face the inside of the sphere 12 at an aperture 43 formed therein remotely from the light source 23, which will illuminate the light-responsive element 40 simultaneously with the surface of an article being analysed.

The photometric device 36 is connected, by means of plural electric cables 44, to the input end of the electronic control device 63 as shown diagramatically in FIG. 5, to which it will address, as explained herein below, the measurement data in analog form.

With reference to FIGS. 2 and 3, it should be observed that the opto-mechanical devices 60 of the spectrophotometer 1, as discussed in the foregoing, include no moving parts, by reason of the internal reference (light-responsive element 40) and the surface to be analysed being illuminated at one time by the light source 23.

Thus, the need is avoided for illuminating in timed sequence the article and internal reference, as is the case with prior spectrophotometers.

With reference to FIG. 5, the electronic control device 63 incorporated to the spectrophotometer 1 of this invention will be described next.

Said device is mounted in a conventional manner on two electronic boards, not shown, which are carried in a substantially parallelepipedic box 47, in turn supported inside the case 2 above the collimator 32 and the box-type housing 34 by a plurality of cylindrical posts 48 (see FIG. 2).

The microprocessor 28 is connected, as shown in FIG. 5 which depicts in diagramatic form the entire electronic control device 63, to the input end of the photometric device 36 through an input interface 64. In particular, said interface 64 is an analog-to-digital converter 45 operative to convert into digital form measurement data received in analog form from the photometric device 36 and to supply the data so converted to the microprocessor 28 over a bus line 65.

In accordance with an aspect of this invention, the microprocessor 28 has a first read/write memory 49 referred to as RAM (Random Access Memory) wherein the data supplied to the microprocessor 28 in digital form from the analog-to-digital converter 45 are to be stored.

The microprocessor 28 also includes a second, read-only memory 50, specifically one of the ROM (Read Only Memory) type, holding the programs that are to make the microprocessor 28 operative.

The above-noted memories, 49 and 50, are conventionally connected to the microprocessor 28 via a set of bus lines 51a and 51b.

In accordance with another aspect of this invention, the power required to operate the electronic control device 63, flash bulb 25, and photometric device 36 is supplied from the power source 20 incorporated to the spectrophotometer, inside the chamber 19.

The microprocessor 28 and power source 20 are further and independently connected, input-wise and in a conventional manner not shown, to a connector 52 carried remotely from the reading head 5 on a side wall 53 of the case 2.

Through the connector 52, the power source 20 is recharged and the measurement data stored in the RAM memory 49 are transferred, as enabled by the microprocessor 28, to an external computer (not shown) arranged to further process and use them in the paint recipe outputting step.

Consent to measurement taking, as given by the microprocessor 28, and the power source 20 charging, can be monitored externally, respectively by means of a light indicator 54 and a galvanometer 55 which are mounted to the reading head 5 of the spectrophotometer, on opposed sides of the handle 3 (see FIG. 4).

The operation of the spectrophotometer 1 according to the invention, will be now described with reference to FIG. 2, which shows its opto-mechanical devices 60.

When the color of an article of manufacture (such as the bodywork of a car) is to be analysed for the purpose of reconstructing or checking it, after turning on the spectrophotometer, one should remove the protection cover 7 from the reading eye 8 and lay the reading head 5 against the surface of the article to be analysed.

In order to take a correct reading of the color, the axis of the reading eye 8 is to be held as perpendicular to the article surface as possible. This operation is made easier, in the instance of ferrous surfaces, by the ring magnet 9 affording proper adhesion of the reading head 5 on the article.

The color analysis is then carried out by depressing the key 61 which straddles the handle 3.

In this way, the light source 23 will be activated by the microprocessor 28 through the control circuit 27. The light source emits, through the flash bulb 25, a flash of light which illuminates the interior of the hollow sphere 12 using energy supplied to it by the power source 20. The sphere 12, which is white-enamelled inside, is effective to make the density of the luminuous flux exiting the reading eye 8 more uniform, which luminous flux will then illuminate in a uniform manner the surface of the colored article of manufacture being analysed.

The light-responsive element 40 of the optical device 39 will be illuminated, by virtue of its peculiar location on the sphere 12, by the flash issuing from the light source 25 at the same time as the article surface is illuminated.

The light reflected back from the thus illuminated surface is then focused by the collimator 32 on the diffraction grating 33 which will scatter its spectral components across a band between 400 and 700 nm, and reflect them, following further focusing by the objective 37, onto the photocells of the photometric device 36. It should be noted that the latter is also simultaneously illuminated by the flash generated by the bulb 25 thanks to the provision of the optical device 39.

The light emission from the bulb 25 reaches, in fact, the photometric device 36 directly through the fiber optics 42, arriving at two sets of photocells respectively illuminated with spectral components having wavelengths within the ranges of 410 to 440 nm and 600 to 640 nm.

The photometric device 36 will then supply the analog-to-digital converter 45 (over the cables 44) with data in analog form relating to the measurement of the reflected light from the sample and the light emitted from the light source 23. The analog-to-digital converter 45 will then convert the input signals from the analog into the digital form, and thereafter pass them to the microprocessor 28 over the bus 65. The microprocessor then stores in its RAM memory 49 the data relating to the double reading thus taken.

Where the color of a different article of manufacture is to be analysed, it will be sufficient to go through the same operations as described so far, taking care on the occasion of each measurement to hold the reading head 5 as perpendicular as feasible to the surface of the article.

In accordance with an aspect of this invention, all of the operation steps of the spectrophotometer 1 as aforesaid can be carried out with no connection to power sources external of the instrument, and using no external control units.

The measurement data are, in fact, stored directly in the RAM memory 49 of the microprocessor 28, and it is only at a later time that they are transferred serially, via the connector 52, into a bench-mounted computer for further processing.

Owing to the simple and robust construction features, and low energy consumption, provided the spectrophotometer of this invention advantageously enables an analysis of colors to be reproduced and/or checked directly in the field, in a fully unattached way and without any connections to external power supply units.

It is to be noted in this respect that, thanks to the presence of the RAM memory 49, the spectrophotometer 1 enables reiterate measurement taking on the colors of one and the same or several articles of manufacture. The measurement data would be first stored in the memory 49 and only later transferred, on return to the workshop or laboratory, into a computer pre-arranged for their further processing.

Furthermore, the spectrophotometer of this invention, thanks to a sensible use of low-cost materials which are readily available on the market, affords the additional important advantage of being quite low in cost and, at last, within the reach of a wide panel of potential users.

Accordingly, it lends itself advantageously to large volume marketing, no longer restricted to but few sophisticated specialized laboratories.

I claim:

1. A portable spectrophotometer comprising:
   a holding case including, all located inside said case:
   a light source connected, via a control circuit, to an output of a microprocessor having data and program storages;
   a sphere for making the luminous flux from the light source exiting said case more uniform;
   a spectroscope for spectrum-wise scattering of reflected light from a sample located adjacent to said sphere illuminated by said light source through said sphere to a photometric device connected to an input end of said microprocessor via an analog-to-digital converter;
   an optical device for illuminating said photometric device directly from said light source simultaneously with lighting of the sample being analyzed;
   a self-contained power supply to the light source, photometric device, control circuit, analog-to-digital converter, and microprocessor; and
   a connector for connecting the microprocessor and power supply to the outside of said case.

2. A spectrophotometer according to claim 1, characterized in that said power supply comprises a storage battery.

* * * * *